(12) United States Patent
Lorenzo (10) Patent No.: US 11,957,354 B2
(45) Date of Patent: Apr. 16, 2024

(54) ANEURYSM IMPLANT SUPPORT DEVICE

(71) Applicant: DePuy Synthes Products, Inc., Raynham, MA (US)

(72) Inventor: Juan Lorenzo, Davie, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 310 days.

(21) Appl. No.: 17/160,570

(22) Filed: Jan. 28, 2021

(65) Prior Publication Data
US 2021/0244419 A1 Aug. 12, 2021

Related U.S. Application Data

(60) Provisional application No. 62/972,427, filed on Feb. 10, 2020.

(51) Int. Cl.
*A61B 17/12* (2006.01)
*A61B 90/00* (2016.01)
(Continued)

(52) U.S. Cl.
CPC .. *A61B 17/12113* (2013.01); *A61B 17/12118* (2013.01); *A61B 17/12172* (2013.01);
(Continued)

(58) Field of Classification Search
CPC .. A61F 2/856; A61F 2/90; A61F 2/954; A61F 2002/823; A61F 2250/0039;
(Continued)

(56) References Cited

U.S. PATENT DOCUMENTS 6,391,037 B1 5/2002 Greenhalgh
6,673,106 B2 1/2004 Mitelberg et al.
(Continued)

FOREIGN PATENT DOCUMENTS

DE   10 2008 028308 A1   4/2009
WO   WO 2011/130579 A1   10/2011

OTHER PUBLICATIONS

European Search Report issued in European Patent Application No. 21 15 5926 dated May 25, 2021.

*Primary Examiner* — Sarah A Long
*Assistant Examiner* — Raihan R Khandker
(74) *Attorney, Agent, or Firm* — TROUTMAN PEPPER HAMILTON SANDERS LLP (57) ABSTRACT

An aneurysm implant support device for treating an aneurysm at a bifurcation can include a body having a tubular lattice extending from an upper body section, through a mid body section, and to a lower body section. The upper body section can be sized, shaped, and otherwise configured for implantation in an aneurysm sac. The upper body section can include support elements positioned at the aneurysm neck which inhibit the embolic implants from exiting the aneurysm. The mid body section can have two large cell openings substantially larger than the cell openings over a majority of the tubular lattice. The two large cell openings can be placed across passageways from a stem blood vessel to branch blood vessels of the bifurcation. The lower body section can be sized, shaped, and otherwise configured to anchor within the stem blood vessel.

17 Claims, 7 Drawing Sheets

(51) Int. Cl.
*A61F 2/856* (2013.01)
*A61F 2/90* (2013.01)
*A61F 2/954* (2013.01)
*A61F 2/82* (2013.01)

(52) U.S. Cl.
CPC .............. *A61B 90/39* (2016.02); *A61F 2/856* (2013.01); *A61F 2/90* (2013.01); *A61B 17/1214* (2013.01); *A61B 2090/3966* (2016.02); *A61F 2002/823* (2013.01); *A61F 2/954* (2013.01); *A61F 2250/0039* (2013.01); *A61F 2250/0098* (2013.01)

(58) Field of Classification Search
CPC ....... A61F 2250/0098; A61B 17/12118; A61B 17/12172; A61B 17/1214
See application file for complete search history.

(56) References Cited

U.S. PATENT DOCUMENTS

| | | | |
|---|---|---|---|
| 9,232,992 | B2 | 1/2016 | Heidner |
| 9,532,792 | B2 | 1/2017 | Galdonik et al. |
| 9,532,873 | B2 | 1/2017 | Kelley |
| 9,533,344 | B2 | 1/2017 | Monetti et al. |
| 9,539,011 | B2 | 1/2017 | Chen et al. |
| 9,539,022 | B2 | 1/2017 | Bowman |
| 9,539,122 | B2 | 1/2017 | Burke et al. |
| 9,539,382 | B2 | 1/2017 | Nelson |
| 9,549,830 | B2 | 1/2017 | Bruszewski et al. |
| 9,554,805 | B2 | 1/2017 | Tompkins et al. |
| 9,561,125 | B2 | 2/2017 | Bowman et al. |
| 9,572,982 | B2 | 2/2017 | Burnes et al. |
| 9,579,484 | B2 | 2/2017 | Barnell |
| 9,585,642 | B2 | 3/2017 | Dinsmoor et al. |
| 9,615,832 | B2 | 4/2017 | Bose et al. |
| 9,615,951 | B2 | 4/2017 | Bennett et al. |
| 9,622,753 | B2 | 4/2017 | Cox |
| 9,636,115 | B2 | 5/2017 | Henry et al. |
| 9,636,439 | B2 | 5/2017 | Chu et al. |
| 9,642,675 | B2 | 5/2017 | Werneth et al. |
| 9,655,633 | B2 | 5/2017 | Leynov et al. |
| 9,655,645 | B2 | 5/2017 | Staunton |
| 9,655,989 | B2 | 5/2017 | Cruise et al. |
| 9,662,129 | B2 | 5/2017 | Galdonik et al. |
| 9,662,238 | B2 | 5/2017 | Dwork et al. |
| 9,662,425 | B2 | 5/2017 | Lilja et al. |
| 9,668,898 | B2 | 6/2017 | Wong |
| 9,675,477 | B2 | 6/2017 | Thompson |
| 9,675,782 | B2 | 6/2017 | Connolly |
| 9,676,022 | B2 | 6/2017 | Ensign et al. |
| 9,692,557 | B2 | 6/2017 | Murphy |
| 9,693,852 | B2 | 7/2017 | Lam et al. |
| 9,700,262 | B2 | 7/2017 | Janik et al. |
| 9,700,399 | B2 | 7/2017 | Acosta-Acevedo |
| 9,717,421 | B2 | 8/2017 | Griswold et al. |
| 9,717,500 | B2 | 8/2017 | Tieu et al. |
| 9,717,502 | B2 | 8/2017 | Teoh et al. |
| 9,724,103 | B2 | 8/2017 | Cruise et al. |
| 9,724,526 | B2 | 8/2017 | Strother et al. |
| 9,750,565 | B2 | 9/2017 | Bloom et al. |
| 9,757,260 | B2 | 9/2017 | Greenan |
| 9,764,111 | B2 | 9/2017 | Gulachenski |
| 9,770,251 | B2 | 9/2017 | Bowman et al. |
| 9,770,577 | B2 | 9/2017 | Li et al. |
| 9,775,621 | B2 | 10/2017 | Tompkins et al. |
| 9,775,706 | B2 | 10/2017 | Paterson et al. |
| 9,775,732 | B2 | 10/2017 | Khenansho |
| 9,788,800 | B2 | 10/2017 | Mayoras, Jr. |
| 9,795,391 | B2 | 10/2017 | Saatchi et al. |
| 9,801,980 | B2 | 10/2017 | Karino et al. |
| 9,808,599 | B2 | 11/2017 | Bowman et al. |
| 9,833,252 | B2 | 12/2017 | Sepetka et al. |
| 9,833,604 | B2 | 12/2017 | Lam et al. |
| 9,833,625 | B2 | 12/2017 | Waldhauser et al. |
| 2006/0064151 | A1 | 3/2006 | Guterman |
| 2008/0281350 | A1 | 11/2008 | Sepetka |
| 2010/0324649 | A1 | 12/2010 | Mattsson |
| 2011/0184452 | A1* | 7/2011 | Huynh ............ A61B 17/12172 606/195 |
| 2012/0283768 | A1 | 11/2012 | Cox et al. |
| 2014/0121752 | A1* | 5/2014 | Losordo .................. A61F 2/954 623/1.35 |
| 2014/0135812 | A1 | 5/2014 | Divino et al. |
| 2014/0200607 | A1 | 7/2014 | Sepetka et al. |
| 2015/0250628 | A1* | 9/2015 | Monstadt ......... A61B 17/12118 623/1.16 |
| 2017/0007264 | A1 | 1/2017 | Cruise et al. |
| 2017/0007265 | A1 | 1/2017 | Guo et al. |
| 2017/0020670 | A1 | 1/2017 | Murray et al. |
| 2017/0020700 | A1 | 1/2017 | Bienvenu et al. |
| 2017/0027640 | A1 | 2/2017 | Kunis et al. |
| 2017/0027692 | A1 | 2/2017 | Bonhoeffer et al. |
| 2017/0027725 | A1 | 2/2017 | Argentine |
| 2017/0035436 | A1 | 2/2017 | Morita |
| 2017/0035567 | A1 | 2/2017 | Duffy |
| 2017/0042548 | A1 | 2/2017 | Lam |
| 2017/0049596 | A1 | 2/2017 | Schabert |
| 2017/0071737 | A1 | 3/2017 | Kelley |
| 2017/0072452 | A1 | 3/2017 | Monetti et al. |
| 2017/0079671 | A1 | 3/2017 | Morero et al. |
| 2017/0079680 | A1 | 3/2017 | Bowman |
| 2017/0079766 | A1 | 3/2017 | Wang et al. |
| 2017/0079767 | A1 | 3/2017 | Leon-Yip |
| 2017/0079812 | A1 | 3/2017 | Lam et al. |
| 2017/0079817 | A1 | 3/2017 | Sepetka et al. |
| 2017/0079819 | A1 | 3/2017 | Pung et al. |
| 2017/0079820 | A1 | 3/2017 | Lam et al. |
| 2017/0086851 | A1 | 3/2017 | Wallace et al. |
| 2017/0086996 | A1 | 3/2017 | Peterson et al. |
| 2017/0095259 | A1 | 4/2017 | Tompkins et al. |
| 2017/0100126 | A1 | 4/2017 | Bowman et al. |
| 2017/0100141 | A1 | 4/2017 | Morero et al. |
| 2017/0100143 | A1 | 4/2017 | Granfield |
| 2017/0100183 | A1 | 4/2017 | Iaizzo et al. |
| 2017/0113023 | A1 | 4/2017 | Steingisser et al. |
| 2017/0147765 | A1 | 5/2017 | Mehta |
| 2017/0151032 | A1 | 6/2017 | Loisel |
| 2017/0165062 | A1 | 6/2017 | Rothstein |
| 2017/0165065 | A1 | 6/2017 | Rothstein et al. |
| 2017/0165454 | A1 | 6/2017 | Tuohy et al. |
| 2017/0172581 | A1 | 6/2017 | Bose et al. |
| 2017/0172766 | A1 | 6/2017 | Vong et al. |
| 2017/0172772 | A1 | 6/2017 | Khenansho |
| 2017/0189033 | A1 | 7/2017 | Sepetka et al. |
| 2017/0189035 | A1 | 7/2017 | Porter |
| 2017/0215902 | A1 | 8/2017 | Leynov et al. |
| 2017/0216484 | A1 | 8/2017 | Cruise et al. |
| 2017/0224350 | A1 | 8/2017 | Shimizu et al. |
| 2017/0224355 | A1 | 8/2017 | Bowman et al. |
| 2017/0224467 | A1 | 8/2017 | Piccagli et al. |
| 2017/0224511 | A1 | 8/2017 | Dwork et al. |
| 2017/0224953 | A1 | 8/2017 | Tran et al. |
| 2017/0231749 | A1 | 8/2017 | Perkins et al. |
| 2017/0252064 | A1 | 9/2017 | Staunton |
| 2017/0265983 | A1 | 9/2017 | Lam et al. |
| 2017/0281192 | A1 | 10/2017 | Tieu et al. |
| 2017/0281331 | A1 | 10/2017 | Perkins et al. |
| 2017/0281344 | A1 | 10/2017 | Costello |
| 2017/0281909 | A1 | 10/2017 | Northrop et al. |
| 2017/0281912 | A1 | 10/2017 | Melder et al. |
| 2017/0290593 | A1 | 10/2017 | Cruise et al. |
| 2017/0290654 | A1 | 10/2017 | Sethna |
| 2017/0296324 | A1 | 10/2017 | Argentine |
| 2017/0296325 | A1 | 10/2017 | Marrocco et al. |
| 2017/0303939 | A1 | 10/2017 | Greenhalgh et al. |
| 2017/0303942 | A1 | 10/2017 | Greenhalgh et al. |
| 2017/0303947 | A1 | 10/2017 | Greenhalgh et al. |
| 2017/0303948 | A1 | 10/2017 | Wallace et al. |
| 2017/0304041 | A1 | 10/2017 | Argentine |
| 2017/0304097 | A1 | 10/2017 | Corwin et al. |
| 2017/0304595 | A1 | 10/2017 | Nagasrinivasa et al. |
| 2017/0312109 | A1 | 11/2017 | Le |
| 2017/0312484 | A1 | 11/2017 | Shipley et al. |

(56) References Cited

U.S. PATENT DOCUMENTS

| | | |
|---|---|---|
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |

\* cited by examiner

```
┌─────────────────────────────────────────────────────────────────────────┐
│  Deliver an implant having a tubular lattice and an interior support    │
│              structure through a catheter to the aneurysm               │
│                                   202                                   │
└─────────────────────────────────────────────────────────────────────────┘
                                    │
                                    ▼
┌─────────────────────────────────────────────────────────────────────────┐
│    Expand a distal portion of the tubular lattice within the sac of     │
│                             the aneurysm                                │
│                                   204                                   │
└─────────────────────────────────────────────────────────────────────────┘
                                    │
                                    ▼
┌─────────────────────────────────────────────────────────────────────────┐
│  Extend the interior support structure within the distal portion of     │
│           the tubular lattice and across the aneurysm neck              │
│                                   206                                   │
└─────────────────────────────────────────────────────────────────────────┘
                                    │
                                    ▼
┌─────────────────────────────────────────────────────────────────────────┐
│  Position a first opening in the tubular lattice across a first         │
│             passageway from a stem vessel to a first branch vessel      │
│                                   208                                   │
└─────────────────────────────────────────────────────────────────────────┘
                                    │
                                    ▼
┌─────────────────────────────────────────────────────────────────────────┐
│  Position a second opening in the tubular lattice across a second       │
│           passageway from the stem vessel to a second branch vessel     │
│                                   210                                   │
└─────────────────────────────────────────────────────────────────────────┘
                                    │
                                    ▼
┌─────────────────────────────────────────────────────────────────────────┐
│  Expand a proximal portion of the tubular lattice within the stem       │
│                             blood vessel                                │
│                                   212                                   │
└─────────────────────────────────────────────────────────────────────────┘
                                    │
                                    ▼
┌─────────────────────────────────────────────────────────────────────────┐
│  Deliver an embolic implant through the tubular lattice and into the    │
│                             aneurysm sac                                │
│                                   214                                   │
└─────────────────────────────────────────────────────────────────────────┘
                                    │
                                    ▼
┌─────────────────────────────────────────────────────────────────────────┐
│  Support the embolic implant at the aneurysm neck with the interior     │
│                              support structure                          │
│                                   216                                   │
└─────────────────────────────────────────────────────────────────────────┘
```

*Figure 10*

ANEURYSM IMPLANT SUPPORT DEVICE

CROSS REFERENCE TO RELATED APPLICATIONS

This application claims the benefit of priority under the Paris Convention as well as 35 U.S.C. §§ 119 and 120 to prior filed U.S. Provisional Patent Application No. 62/972,427 filed on Feb. 10, 2020 which is hereby incorporated by reference as set forth in full herein.

FIELD OF INVENTION

The present invention relates generally to implantable structures for placement in proximity to an opening or cavity in a physiological structure, such as the neck of an aneurysm, using minimally invasive techniques, and to methods of making and deploying such structures. In one aspect, the implantable structures described herein contact and support tissue in proximity to the opening or cavity.

BACKGROUND

Aneurysms are bulges in an artery wall, generally caused by a weakening in the artery wall, that form an opening or cavity and are often the site of internal bleeding and stroke. In general, the minimally invasive therapeutic objective is to prevent material that collects or forms in the cavity from entering the bloodstream, and to prevent blood from entering and collecting in the aneurysm. This is often accomplished by introducing various materials and devices into the aneurysm. One type of aneurysm, commonly known as a "wide neck aneurysm" is known to present particular difficulty in the placement and retention of vaso-occlusive coils. Wide neck aneurysms are generally referred to as aneurysms of vessel walls having a neck or an entrance zone from the adjacent vessel that is large compared to the diameter of the aneurysm or that is clinically observed to be too wide to effectively retain vaso-occlusive coils deployed using the techniques discussed above. When treating sidewall aneurysms, stents can be placed across the neck of the aneurysm to prevent embolic material from exiting the aneurysm neck. Known stents include the Enterprise® line of self-expanding stents, which are described in numerous patents and published patent applications including U.S. Pat. No. 6,673,106 which is hereby incorporated by reference hereinto. Treating a "wide neck aneurysm" at a bifurcation is further complicated as a stent placed across an aneurysm at a bifurcation can block one or more of the blood vessel passageways.

SUMMARY

An example method for treating an aneurysm at a bifurcation can include some or all of the following steps executed in a variety of orders and can include fewer or additional steps as understood by a person of ordinary skill in the art according to the teachings of the present disclosure. The bifurcation being treated by the example method can include a first passageway from a stem blood vessel to a first branch blood vessel and a second passageway from the stem blood vessel to a second branch blood vessel. The aneurysm being treated by the example method can be positioned opposite the stem blood vessel and between the first and second passageways.

The method can include delivering an implant comprising a tubular lattice and an interior support structure through a catheter to the aneurysm.

The method can include expanding a distal portion of the tubular lattice within the sac of the aneurysm.

The method can include extending the interior support structure within the distal portion of the tubular lattice and across the aneurysm neck.

The method can include positioning a first opening in the tubular lattice across the first passageway. The first opening can have a first cross sectional area defined by the perimeter of the first opening. The first cross sectional area can extend across a majority of the first passageway.

The method can include positioning a second opening in the tubular lattice across the second passageway. The second opening can have a second cross sectional area defined by the perimeter of the second opening. The second cross sectional area can extend across a majority of the second passageway.

The method can include expanding a proximal portion of the tubular lattice within the stem blood vessel.

The method can include delivering an embolic implant through the tubular lattice and into the aneurysm sac.

The method can include supporting the embolic implant at the aneurysm neck with the interior support structure.

An example embolic implant support device including a proximal end, a distal end, a lower body section, an upper body section, and a mid body section. The lower body section extends distally from the proximal end. The upper body section extends proximally from the distal end. The mid body section extends between the lower body section and the upper body section.

The lower body section, the upper body section, and the mid body section can include a tubular lattice extending longitudinally between the proximal end and the distal end. The tubular lattice can include a first large cell opening and a second large cell opening each positioned in the mid body section. The first and second large cell openings can be positioned opposite each other.

The upper body section can have a first diameter measured near the proximal end of the device. A majority of the tubular lattice can have a second diameter. The lower body section can have a third diameter measured near the distal end of the device. The first diameter can be greater than the second diameter. The third diameter can be greater than the second diameter.

The majority of the tubular lattice can have cells of substantially uniform cell size. Each of the first and second large cell openings respectively can have a cell opening that is larger than the uniform cell size. Specifically, the large cell openings can be about ten times the substantially uniform cell size, at least three times the substantially uniform cell size, or between about three times and about one hundred times the substantially uniform cell size. The tubular lattice can have at least three cells with the substantially uniform cell size. The tubular lattice can have between three and about twenty-six cells with the substantially uniform cell size.

The tubular lattice can have two narrow sections separating the first and second large cell openings. Each of the two narrow sections can extend longitudinally across the mid body section to connect the upper body section and the lower body section.

The device can further include one or more proximal radiopaque markers attached to the tubular lattice approximate the proximal end.

The device can further include one or more mid radiopaque markers attached to the tubular lattice within the mid body section.

The device can further include one or more distal radiopaque markers attached to the tubular lattice approximate the distal end.

The device can further include a support member extending across a lumen through the tubular lattice and within the upper body section.

The device can further include two arcuate struts extending across a lumen through the tubular lattice and affixed to the upper body section, each of the two arcuate struts comprising a curvature extending proximally toward the mid body section and crossing each other at approximately a 90 degree angle. The aforementioned support member can include one or both of the two arcuate struts.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

FIGS. 1 through 9 illustrate an embolic implant support device 100 in various orientations and at various stages of implantation as described in greater detail below. Each of FIGS. 1 through 9 includes cartesian axes (x axis, y axis, and z axis) to aid in visualizing the three dimensional structure of the device 100. The implant support device 100 includes a body 106 generally aligned longitudinally parallel to the y axis, large cell openings 118, 120 generally aligned parallel to the x axis, and narrow connecting segments 119, 121 generally aligned parallel to the z axis.

Figure 1:
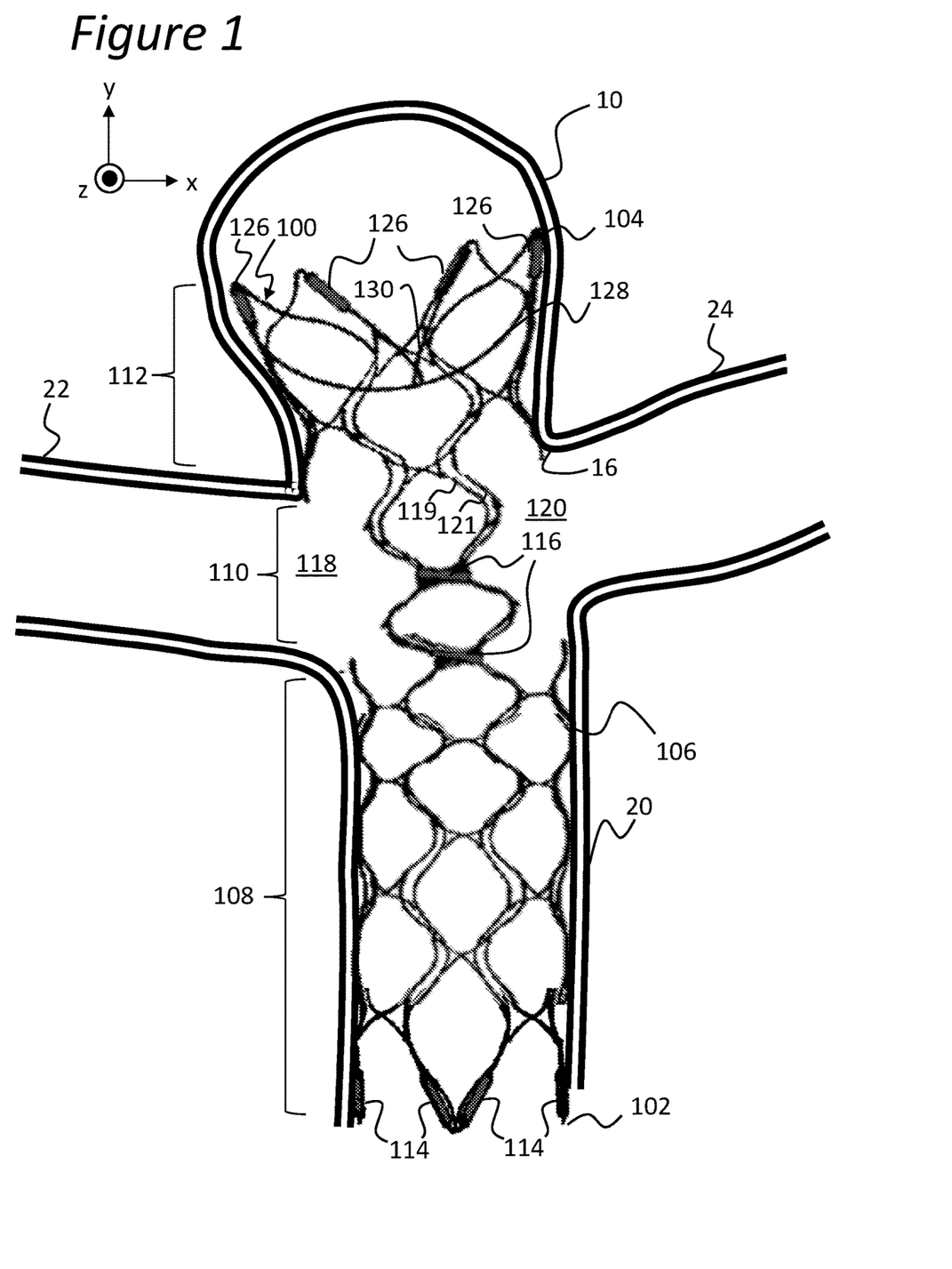
FIG. 1 is an illustration of an embolic implant support device implanted as part of an aneurysm treatment at a bifurcation according to aspects of the present invention.
Figure 2:
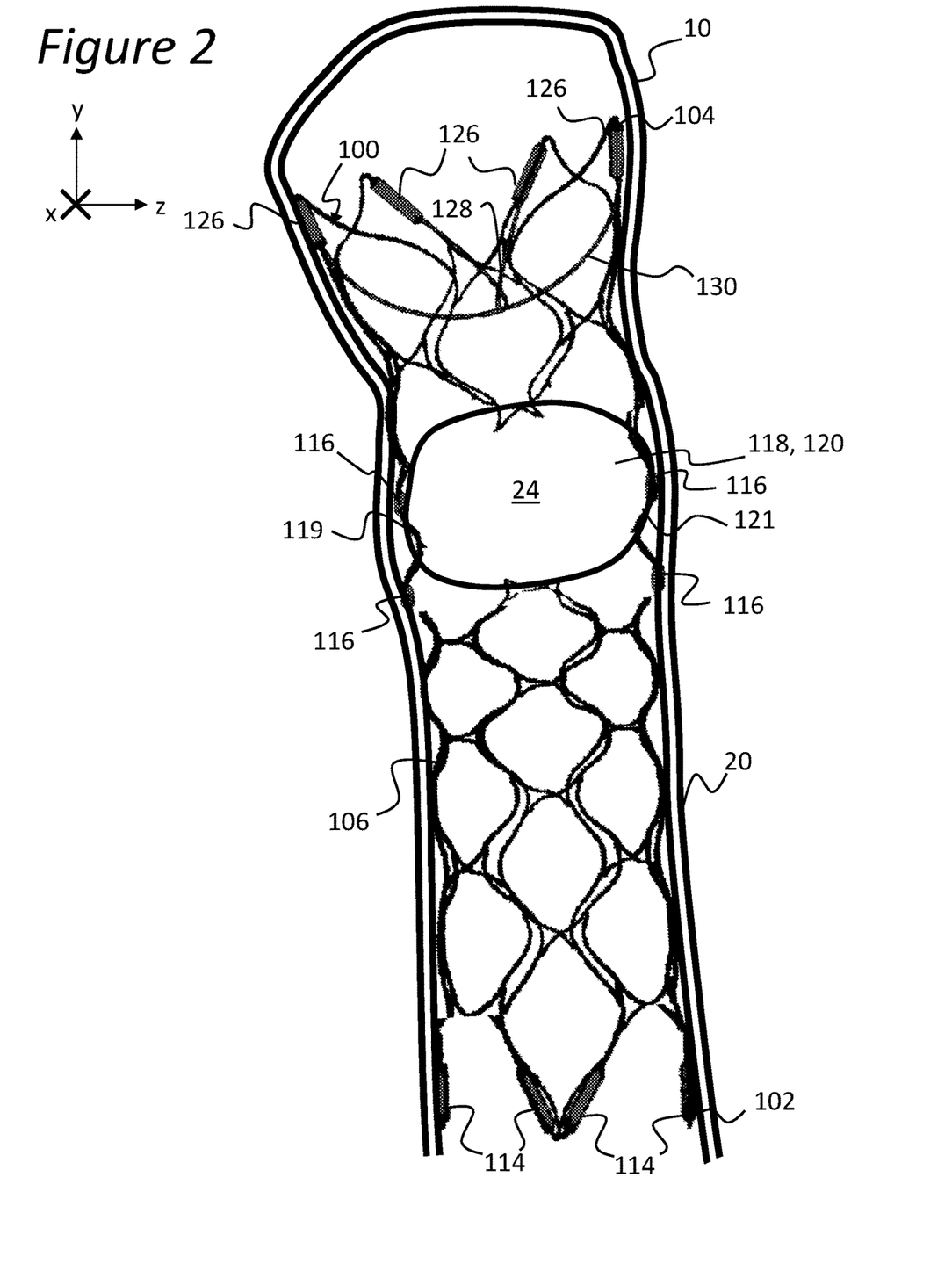
FIG. 2 is an illustration of a side view of support device implanted as part of an aneurysm treatment at a bifurcation according to aspects of the present invention.

FIGS. 1 and 2 are illustrations of the embolic implant support device 100 implanted as part of an aneurysm treatment at a bifurcation. FIGS. 1 and 2 are orthogonal views of a treatment site with the vasculature and aneurysm cross-sectioned for illustration purposes.

The support device 100 can have radiopaque markers 126, 116, 114 attached to the body 106, and support elements 128, 130 extending across the interior of the body 106. The body 106 can include a tubular lattice formed by laser cutting a hypotube or formed by other means appropriate for manufacturing a stent. The tubular lattice can include materials that allow the lattice to self-expand upon exiting a delivery catheter or delivery tube near the treatment site. For instance, the tubular lattice can include nickel titanium. The tubular lattice can extend from a proximal end 102 of the device 100 to a distal end 104 of the device.

When implanted as illustrated, an upper body section 112 of the device 100 can be positioned within an aneurysm 10 (i.e. within the aneurysm sac), the support elements 128, 130 can extend across the aneurysm sac near the neck 16, a mid body section 110 of the device 100 can be positioned across passageways from a stem blood vessel 20 to a first branch vessel 22 and a second branch vessel 24, and a lower body section 108 can be positioned within the stem blood vessel 20. Each of the upper body section 112, mid body section 110, and lower body section 108 can have different cell geometry and strut configuration.

The upper body can be positioned such that the distal end of the upper body is near, or distal to, the aneurysm neck 16. The upper body section 112 can be shaped to conform to an inner surface of a substantially spherical cavity such as the inner walls of the aneurysm 10 as illustrated. The device 100 can include distal radiopaque markers 126 attached to the upper body section 112 near the distal end 104 of the device 100. The distal radiopaque markers 126 can aid in the visualization of the distal end 104 of the device 100 during treatment. The supporting elements 128, 130 can be attached to the upper body section 112. Ends of the supporting elements 128, 130 can be attached to the distal markers 126. The distal markers 126 can serve as fasteners for attaching supporting elements 128, 130 to the upper body section 112 (e.g. bands crimping struts of the tubular lattice of the upper body section 112 to the supporting elements 128, 130). The supporting elements 128, 130 can bow in the proximal direction in relation to the distal end 104 of the device to form a cup or bowl shaped frame near the aneurysm neck 16. The supporting elements 128, 130 cross the aneurysm neck 16. The supporting elements can be positioned, constructed, and otherwise configured to support embolic coils or other embolic implants subsequently inserted in the aneurysm sac.

The mid body section 110 can include first and second large cell openings 118, 120. The first and second large cell openings 118, 120 can be positioned opposite each other. The first large cell opening 118 can be positioned in a first passageway from the stem blood vessel 20 to the first branch vessel 22. The second large cell opening 120 can be positioned in a second passageway from the stem blood vessel 20 to the second branch vessel 24. The large cell openings 118, 120 can be designed to allow uninterrupted blood flow through the passageways to the branch vessels 22, 24.

Each of the first and second large cell openings 118, 120 can each respectively have a cross sectional area defined by the perimeter of each respective opening. As used herein, "perimeter" extends along the surface of structures of the device (e.g. lattice struts and radiopaque markers) and does not cross structures of the device. In other words, structures of the device 100 do not extend within or through the cross sectional area. The cross sectional areas of each of the first and second large cell openings 118, 120 can extend across a majority of the first and second passageways, respectively. As illustrated, each of the first and second openings 118, 120 area sized and positioned such that passageways from the stem blood vessel 20 to each branch blood vessel 22, 24 are unobstructed by the device 100. In other words, no struts of the tubular lattice of the body 106 extend across the passageways.

The mid body section 110 can further include narrow sections 119, 121 connecting the upper body section 112 to the lower body section 108 and separating the first large cell opening 118 from the second large cell opening 120. The device 100 can include radiopaque markers 116 attached to one or both of the narrow sections 119, 121. The radiopaque markers in the mid body section 110 can aid in orienting the large cell openings 118, 120 across the branch vessel passageways during treatment.

The lower body section 108, when implanted can apply a radial force to vascular walls of the stem blood vessel 20. The lower body section 108 can include proximal radiopaque markers 114. The proximal radiopaque markers 114 can be positioned near the proximal end 102 of the device 100 to aid visualization of the position of the proximal end 102 of the device 100 during a treatment.

Some or all of the proximal radiopaque markers 114, mid body radiopaque markers 116, and proximal radiopaque markers 114 can include marker bands attached to the tubular lattice. Additionally, or alternatively, some or all of the radiopaque markers can have a form and be attached to the body 106 of the device 100 by means known to a person of ordinary skill in the art according to the teachings herein.

Figure 3:
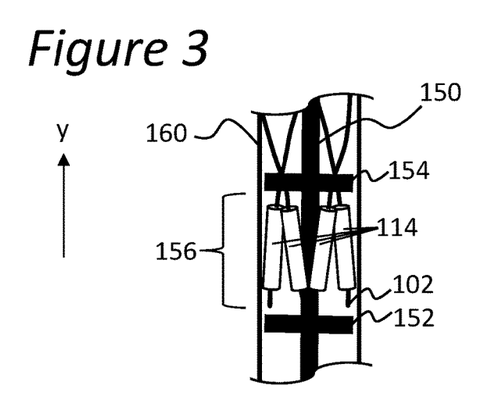
FIG. 3 is an illustration of the proximal end of the support device over a delivery wire in a catheter for delivery according to aspects of the present invention.

FIG. 3 is an illustration of the proximal end 102 of the device 100 over a delivery wire 150 in a catheter 160 for delivery. FIG. 3 illustrates one possible system and method for delivering the device 100. The device 100 can be delivered by several other systems and methods suitable for delivering a stent or other implant as understood by a person of ordinary skill in the art. For instance, the device 100 can be positioned over a delivery wire having a frictional pad thereon such that when the device 100 is constricted in a catheter over the frictional pad, the pad engages the device 100 so that the device 100 can be moved through the catheter by manipulating the delivery wire. As another example, the device 100 can be simply pushed at its proximal end 102 out of a delivery tube or catheter.

Referring again to FIG. 3, the device 100 can be collapsed over the delivery wire 150 and positioned within the catheter 160 such that the proximal markers 114 are confined within a notch 156 in the delivery wire 150. The delivery wire 150, catheter 160, and proximal markers 114 can be each sized such that the proximal markers are confined in a space defined by the notch 156 and the interior of the catheter 160 as the delivery wire 150 (and thereby the device 100) is translated through the catheter 160. The device 100 can be positioned such that the upper body section 112 exits the distal end of the catheter 160 before the mid body section 110 and the mid body section 110 exits the distal end of the catheter 160 before the lower body section 108.

The delivery wire 150 can include a proximal bump 152 and a distal bump 154 thereon. The notch 156 can be defined by the space between the proximal and distal bumps 152, 154. When the delivery wire 150 is moved distally through the catheter 160, the proximal bump 152 can engage the proximal end 102 of the device 100 to push the device 100 distally. When the delivery wire 150 is moved proximally through the catheter 160, the distal bump 154 can engage the proximal markers 114 to move the device 100 proximally. In some treatments, a partially deployed device 100 can be retracted into the distal end of the catheter 160 by moving the delivery wire 150 proximally.

Figure 4:
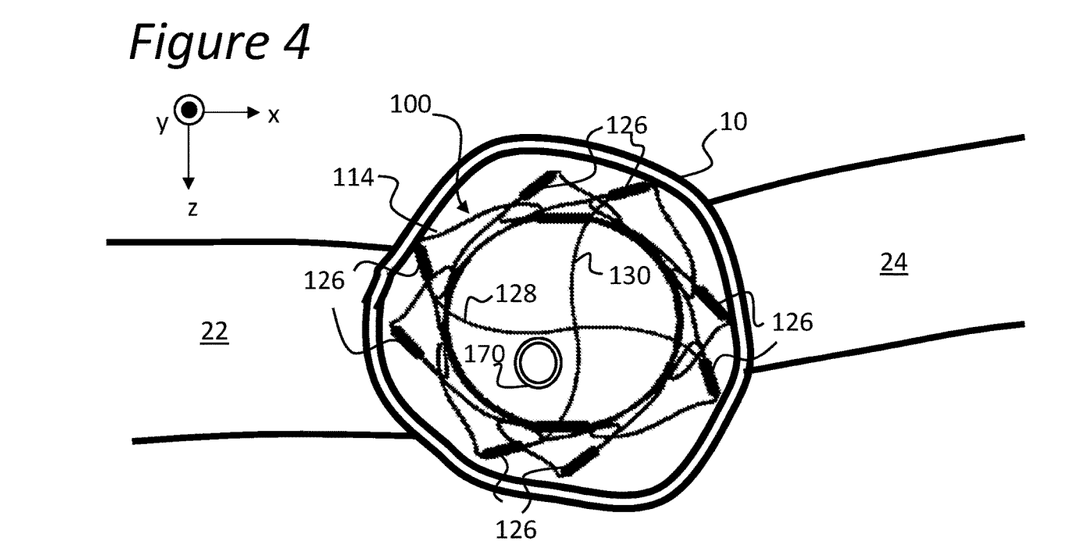
FIG. 4 is an illustration of a top view of the support device implanted and a distal end of an embolic implant delivery tube positioned to deliver an embolic implant as part of an aneurysm treatment at a bifurcation according to aspects of the present invention.

FIG. 4 is an illustration of a top view of the device 100 implanted as illustrated in FIGS. 1 and 2. FIG. 4 further illustrates a distal end of an embolic implant delivery tube 170 positioned within the body 106 of the device. The distal end of the implant delivery tube 170 can be positioned to deliver embolic implants through the frame formed by the supporting elements 128, 130.

Figure 5:
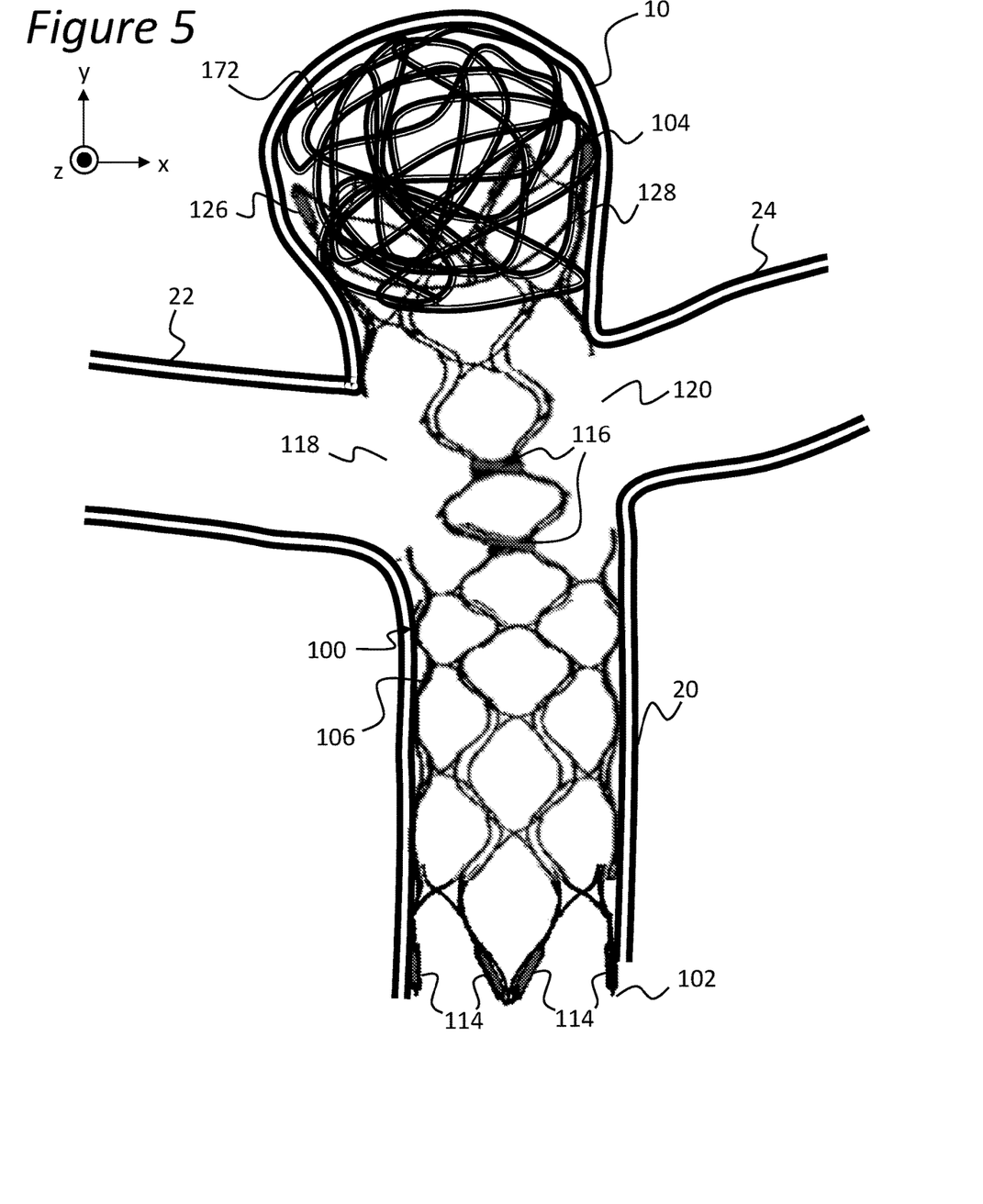
FIG. 5 is an illustration of an aneurysm treated with the support device and an embolic implant according to aspects of the present invention.

FIG. 5 is an illustration of the aneurysm 10 treated with the device 100 and after an embolic implant 172 is delivered through the implant delivery tube 170 illustrated in FIG. 4. The embolic implant 172 can include an embolic coil, embolic braid, and/or other blood clotting implant.

Figure 6:
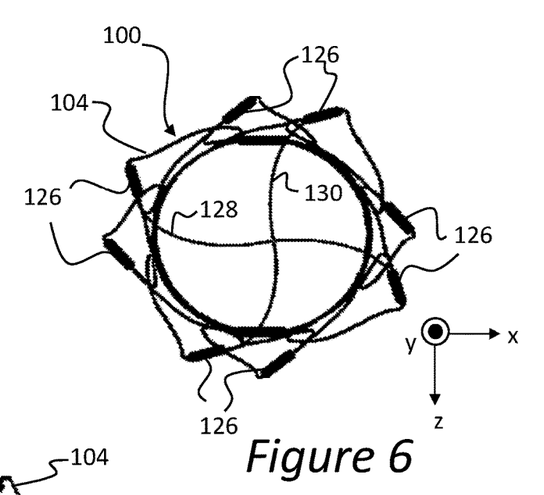
FIG. 6 is an illustration of a top view of the distal end of the support device according to aspects of the present invention.
Figure 7:
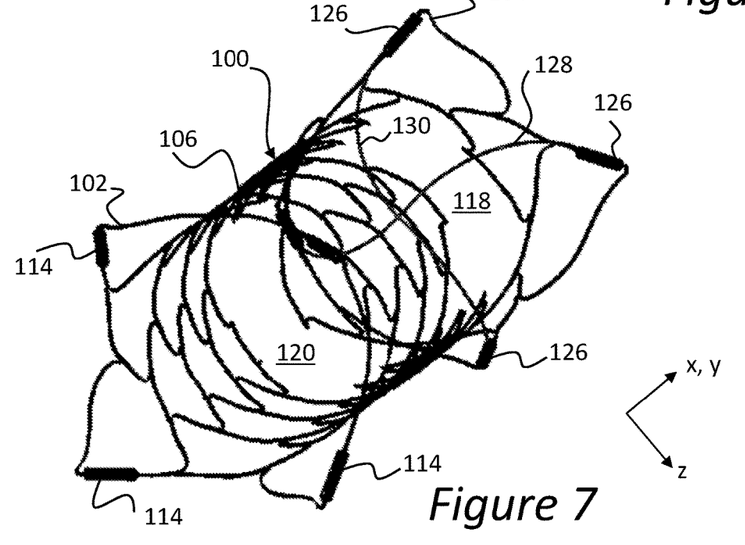
FIG. 7 is an illustration of a perspective view of the support device according to aspects of the present invention.
Figure 8:
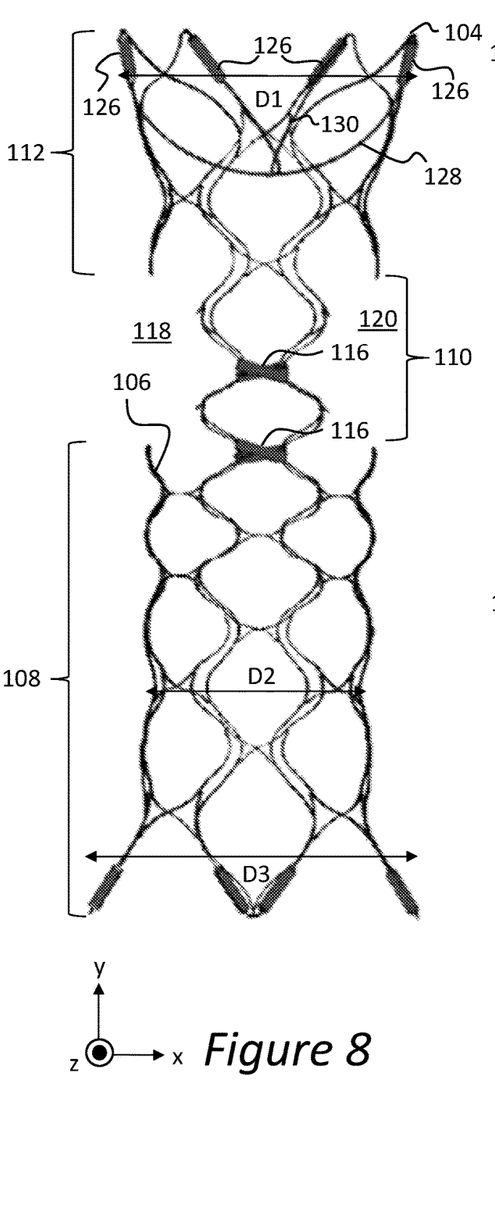
FIG. 8 is an illustration of a side view of the support device according to aspects of the present invention.
Figure 9:
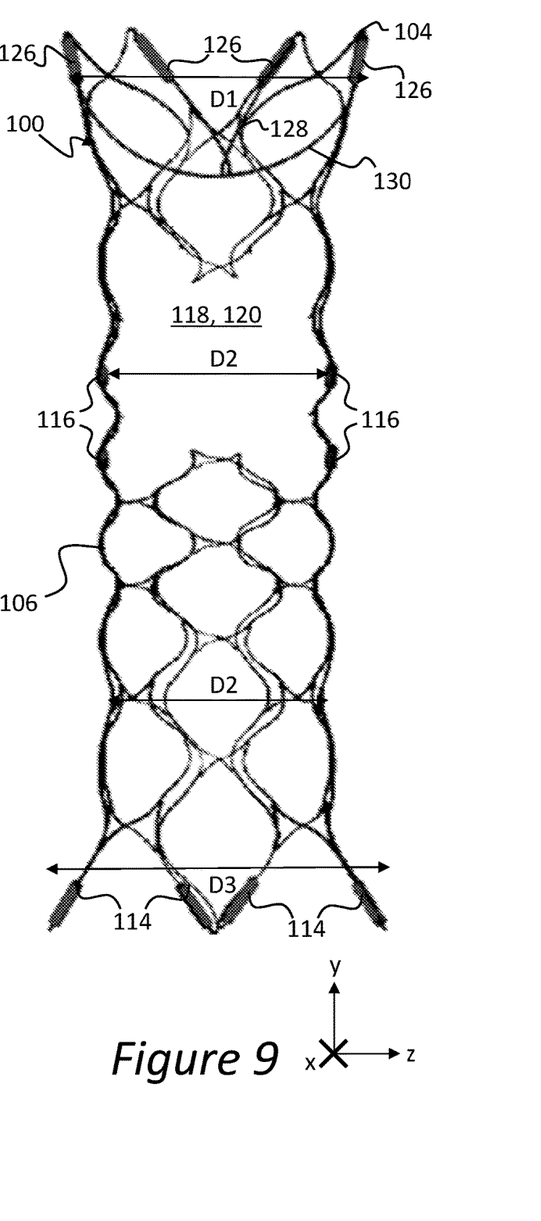
FIG. 9 is an illustration of another side view of the support device according to aspects of the present invention.

FIGS. 6 through 9 are illustrations of the device 100 in an expanded configuration unconfined by anatomy of a treatment site, a delivery catheter, or other confinement. FIG. 6 is an illustration of a top view of the distal end 104 of the support device 100. FIG. 7 is an illustration of a perspective view of the support device 100. FIG. 8 is an illustration of a side view of the support device 100. FIG. 9 is an illustration of another side view of the support device 100.

The device 100 can be self-expanding such that when the device 100 exits the delivery tube 170 at a treatment site, the device 100 tends to expand to the expanded configuration as illustrated in FIGS. 6 through 9. The implanted shape of the device 100 can therefore be based on the expanded configuration and the geometry of the anatomy of the treatment site. Where the device 100 is inhibited from expanding completely, the device 100 can provide outward force to vascular walls, aneurysm walls, and/or other surfaces of the treatment site.

Near the distal end 104 of the device 100, the upper body section 112 can be flared to a distal diameter D1. Near the proximal end 102 of the device, the lower body section 108 can be flared to a proximal diameter D3. Along a majority of the body 106 between the proximal and distal ends 102, 104, the device can have a primary diameter D2. The proximal diameter D3 can be greater than the primary diameter D2. The proximal diameter D3 can be sized to anchor the device to the stem blood vessel 20. The distal diameter D1 can be greater than the primary diameter D2. The distal diameter D1 can be sized to anchor the device 100 within the aneurysm 10. The distal diameter D1 can be about the same, greater than, or less than the proximal diameter D3. The distal diameter D1 can be sized to be appropriate for treating aneurysms having a sac diameter within a predetermined range. The distal diameter D1 can be about equal to or greater than the predetermined range of sac diameters for which the device 100 is configured to treat. The proximal diameter D3 and primary diameter D2 can be sized to be appropriate for placement within a stem blood vessel having a vascular diameter within a predetermined range. The proximal diameter D3 can be larger than the predetermined range of vascular diameters for which the device 100 is configured to treat. The primary diameter D2 can be sized to appose the lower body section 108 to walls of the stem blood vessel 20. The primary diameter D2 can be about equal to or larger than the predetermined range of vascular diameters for which the device 100 is configured to treat.

Referring to FIGS. 1, 2, 5, 8, and 9, the size of the large cell openings 118, 120 is illustrated to be about ten times the size of smaller cells of the tubular lattice. A majority of the upper body section 112 and lower body section 108 includes smaller cells of substantially uniform size. Each narrow section of the mid body section 110 includes about two of the smaller cells positioned longitudinally, distal and proximal to each other. As illustrated, the tubular lattice includes about twenty-six cells having the substantially uniform size. As illustrated in FIG. 9, when viewed from the illustrated side, the large cell openings 118, 120 can span across a majority of the primary diameter D2.

The size of the large cell openings 118, 120 can be sized to treat a certain treatment site geometry. Specifically, the large cell openings 118, 120 can be a factor determining whether or not the device 100 is suitable for treating an aneurysm adjacent branch vessels 22, 24 having a measured entrance size. The large cell opening 118, 120 can be large enough so that each entrance to the branch vessels 22, 24 is unobstructed by the device 100 when implanted. Overly large cell openings 118, 120 may impact structural integrity of the device, making the device 100 more difficult to position and/or anchor.

The size and number of the smaller cells having substantially uniform cell size can impact the structural integrity of the device 100 as understood by a person of ordinary skill in the art. The device 100 can include larger cells of uniform size over a majority of the tubular body than as illustrated, such that the large cell opening is about three times the uniform cell size and still main structural integrity of the device 100 suitable for some aneurysm and treatment site geometries. The device 100 can include smaller cells of uniform size over a majority of the tubular body than as illustrated, such that the large cell opening is more than ten times the uniform cell size and still main structural integrity of the device 100 suitable for some aneurysm and treatment site geometries. Smaller uniform cell size may increase the stiffness and bulk of the device 100, thereby making the device 100 more difficult to position, together with material selection and strut thickness, such factors can determine the minimum practical uniform cell size. Other factors may also affect minimum uniform cell size as appreciated and understood by a person of ordinary skill in the art according to the teachings of the present disclosure. With current materials and fabrication technology, the large cell opening size is preferably between about one hundred times and about three times the size of the uniform cell size. Depending on the specific design factors, the large cell openings may be up about to one thousand times the uniform cell size.

Figure 10:
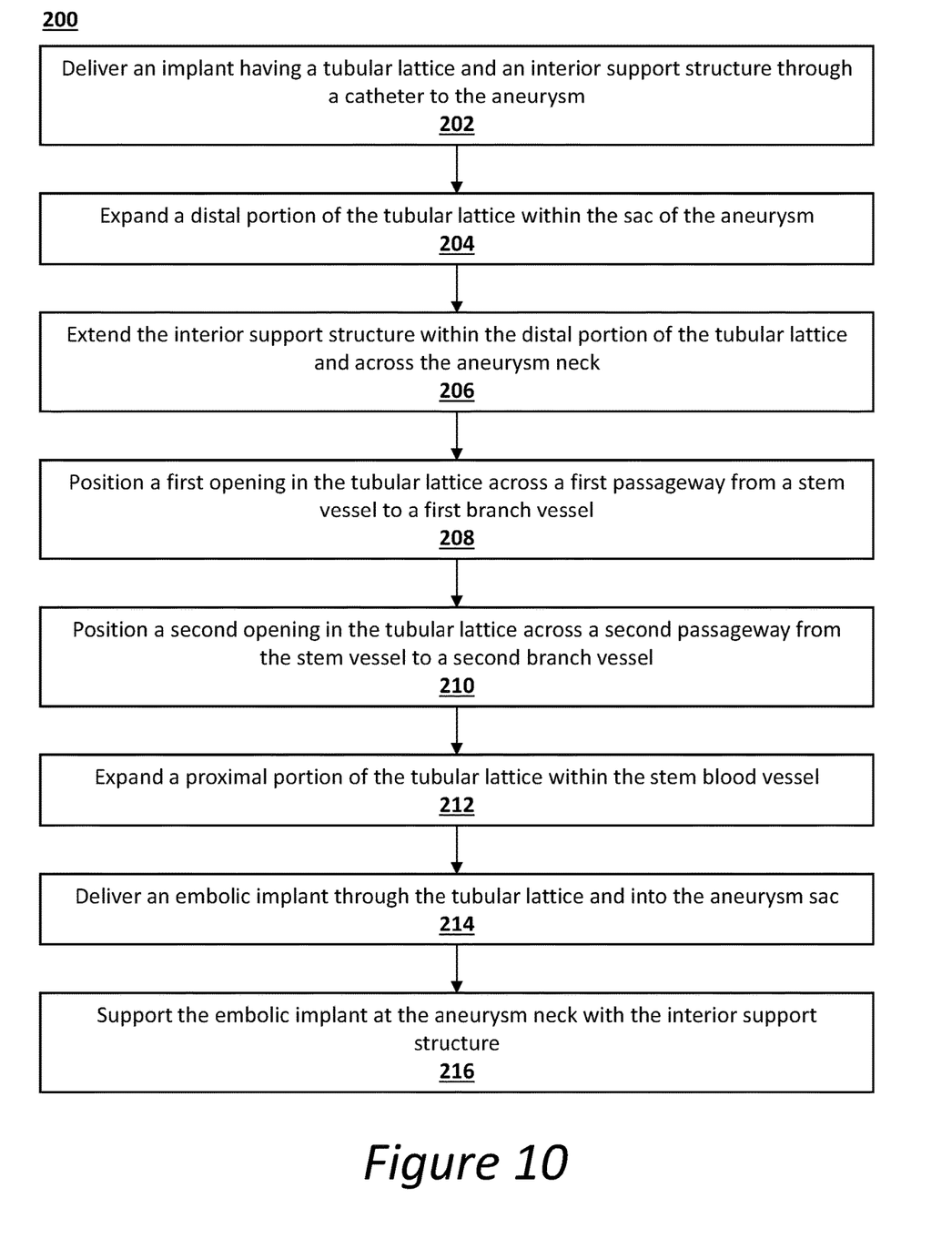
FIG. 10 is a flow diagram of method steps for treating an aneurysm at a bifurcation according to aspects of the present invention.

FIG. 10 illustrates a method 200 for treating an aneurysm 10 at a bifurcation including a stem blood vessel 20, a first branch blood vessel 22, a second branch blood vessel 24 such that the aneurysm 10 is positioned between the branch blood vessels 22, 24 and opposite the stem blood vessel 20. Steps in the illustrated method 200 can be performed in a variety of orders as understood by a person or ordinary skill in the art according to the teachings of the present disclosure. The method 200 can further include steps not illustrated.

At step 202, deliver an implant having a tubular lattice and an interior support structure through a catheter to the aneurysm. The implant can be or include the device 100 illustrated and described herein, an alternative thereto, or variation thereof as understood by a person of ordinary skill in the art according to the teachings of the present disclosure. The be the body 106 (or at least part of the body 106) illustrated and described herein, an alternative thereto, or variation thereof as understood by a person of ordinary skill in the art according to the teachings of the present disclosure. The interior support structure can include the supporting elements 128, 130 illustrated and described herein, alternatives thereto, or variations thereof as understood by a person of ordinary skill in the art according to the teachings of the present disclosure. The implant can be delivered through a catheter such as the catheter 160 illustrated in FIG. 3. The implant can be delivered by methods described herein or other method as understood by a person of ordinary skill in the art according to the teachings of the present disclosure.

At step 204, expand a distal portion of the tubular lattice within the sac of the aneurysm. the distal portion of the tubular lattice can be included in the upper body section 112 of the body 106 of the device 100 illustrated and described herein, an alternative thereto, or variation thereof as understood by a person of ordinary skill in the art according to the teachings of the present disclosure. The distal portion can be self-expandable upon exiting the distal end of the catheter through which the implant is delivered at step 202. The distal end of the catheter can be positioned at the aneurysm neck and directed toward the aneurysm sac when the distal portion is pushed out of the distal end of the catheter.

At step 206, extend the interior support structure within the distal portion of the tubular lattice and across the aneurysm neck. The support structure can be positioned as the supporting elements 128, 130 are illustrated and described herein, an alternative thereto, or variation thereof as understood by a person of ordinary skill in the art according to the teachings of the present disclosure.

At step 208, position a first opening in the tubular lattice across a first passageway from a stem vessel to a first branch vessel. The first opening can have a first cross sectional area defined by the perimeter of the first opening. The first cross sectional area can extend across a majority of the first passageway. Positioned as such, blood flow through the first passageway can be unobstructed by the implant.

At step 210, position a second opening in the tubular lattice across a second passageway from the stem vessel to a second branch vessel. The second opening can have a second cross sectional area defined by the perimeter of the second opening. The second cross sectional area can extend across a majority of the second passageway. Positioned as such, blood flow through the second passageway can be unobstructed by the implant.

Regarding steps 208 and 210, the first and second openings can be positioned as the large cell openings 118, 120 of the device 100 are illustrated and described herein, an alternative thereto, or variation thereof as understood by a person of ordinary skill in the art according to the teachings of the present disclosure. The first and second openings can be positioned on a mid body section of the implant such as the large cell openings 118, 120 are positioned on the mid body section 110 of the device as illustrated and described herein.

At step 212, expand a proximal portion of the tubular lattice within the stem blood vessel. The proximal portion of the tubular lattice can be included in the lower body section 108 of the device 100 as illustrated and described herein, an alternative thereto, or variation thereof as understood by a person of ordinary skill in the art according to the teachings of the present disclosure. The proximal portion can be expanded to appose walls of the stem blood vessel. The proximal portion can be expanded to allow blood to flow freely through the stem blood vessel.

At step 214, deliver an embolic implant through the tubular lattice and into the aneurysm sac. The embolic implant can include the embolic implant 172 illustrated and described herein, an alternative thereto, or variation thereof as understood by a person of ordinary skill in the art according to the teachings of the present disclosure. The embolic implant can be positioned as illustrated in FIG. 5 or otherwise positioned as appreciated and understood by a person of ordinary skill in the art according to the teachings herein. The embolic implant can be delivered through a delivery tube 170 as illustrated in FIG. 4 or other delivery system as understood by a person of ordinary skill in the art according to the teachings of the present disclosure.

At step 216, support the embolic implant at the aneurysm neck with the interior support structure. The embolic implant can be supported as illustrated and described in relation to FIG. 5 as otherwise described herein, an alternative thereto, or variation thereof as understood by a person of ordinary skill in the art according to the teachings of the present disclosure.

The descriptions contained herein are examples of embodiments of the invention and are not intended in any way to limit the scope of the invention. As described herein, the invention contemplates many variations and modifications of the stent, including alternative shapes for the longitudinal elements, interconnecting members having more or fewer branches, interconnecting members having different geometries, additional or fewer struts, or utilizing any of numerous materials or manufacturing means for the stent, for example. These modifications would be apparent to those having ordinary skill in the art to which this invention relates and are intended to be within the scope of the claims which follow.

The invention claimed is:

1. An implant comprising:
    a tubular lattice extending from an open distal end of the implant to an open proximal end of the implant, the tubular lattice comprising:
        a lower body section extending distally from the open proximal end;
        an upper body section extending proximally from the open distal end;
        a mid body section extending between the lower body section and the upper body section;
        a first large cell opening positioned in the mid body section;
        a second large cell opening positioned in the mid body section opposite the first large cell opening; and
        two narrow sections in the mid body section separating the first large cell opening and second large cell opening and extending longitudinally across the mid body section to connect the upper body section and the lower body section, each of the two narrow sections of the mid body section comprising about two smaller cells positioned longitudinally, distal and proximal to each other; and
    a support member extending across a lumen through the tubular lattice and within the upper body section,
    wherein the upper body section comprises a first diameter at the open distal end,
    wherein the lower body section comprises a second diameter extending from a distal end of the lower body section to the open proximal end,
    wherein the lower body section comprises a third diameter at the open proximal end,
    wherein the first diameter is greater than the second diameter, and
    wherein the third diameter is greater than the second diameter.

2. The implant of claim 1,
    wherein a majority of the tubular lattice comprises cells of a substantially uniform cell size, and
    wherein each of the first and second large cell openings respectively comprise a cell opening of at least three times the substantially uniform cell size.

3. The implant of claim 2,
    wherein each of the first and second large cell openings respectively comprise a cell opening of between about three times and about one hundred times the substantially uniform cell size.

4. The implant of claim 3,
    wherein each of the first and second large cell openings respectively comprise a cell opening of about ten times the substantially uniform cell size.

5. The implant of claim 3, wherein the tubular lattice comprises between three and about twenty-six cells comprising the substantially uniform cell size.

6. The implant of claim 1, further comprising:
    one or more proximal radiopaque markers attached to the tubular lattice approximate the open proximal end;
    one or more mid radiopaque markers attached to the tubular lattice within the mid body section; and
    one or more distal radiopaque markers attached to the tubular lattice approximate the open distal end.

7. The implant of claim 1, wherein the support member comprises at least two arcuate struts extending across the lumen through the tubular lattice and affixed to the upper body section, each of the arcuate struts comprising a curvature extending proximally toward the mid body section.

8. The implant of claim 7, wherein the at least two arcuate struts consists of two arcuate struts crossing each other at approximately a 90 degree angle.

9. An implant comprising:
    an open proximal end;
    an open distal end;
    a lower body section extending distally from the open proximal end;
    an upper body section extending proximally from the open distal end; and
    a mid body section extending between the lower body section and the upper body section,
    wherein the lower body section, the upper body section, and the mid body section comprise a tubular lattice extending longitudinally between the open proximal end and the open distal end,
    wherein the tubular lattice comprises:
        a first large cell opening and a second large cell opening each positioned in the mid body section such that the first and second large cell opening are positioned opposite each other; and
        two narrow sections in the mid body section separating the first large cell opening and second large cell opening and extending longitudinally across the mid body section to connect the upper body section and the lower body section, each of the two narrow sections of the mid body section comprising about two smaller cells positioned longitudinally, distal and proximal to each other,
    wherein the upper body section comprises a first diameter at the open distal end,
    wherein the lower body section comprises a second diameter extending from a distal end of the lower body section to the open proximal end,
    wherein the lower body section comprises a third diameter at the open proximal end,
    wherein the first diameter is greater than the second diameter, and
    wherein the third diameter is greater than the second diameter.

10. The implant of claim 9, further comprising:
a support member extending across a lumen through the tubular lattice and within the upper body section.

11. The implant of claim 10, wherein the support member comprises at least two arcuate struts extending across the lumen through the tubular lattice and affixed to the upper body section, each of the arcuate struts comprising a curvature extending proximally toward the mid body section.

12. The implant of claim 11, wherein the at least two arcuate struts consist of two arcuate struts crossing each other at approximately a 90 degree angle.

13. The implant of claim 9,
wherein the majority of the tubular lattice comprises cells of a substantially uniform cell size, and
wherein each of the first and second large cell openings respectively comprise a cell opening of between about three times and about one hundred times the substantially uniform cell size.

14. The implant of claim 13, wherein the tubular lattice comprises between three and about twenty-six cells comprising the substantially uniform cell size.

15. The implant of claim 9, further comprising:
one or more proximal radiopaque markers attached to the tubular lattice approximate the open proximal end;
one or more mid radiopaque markers attached to the tubular lattice within the mid body section; and
one or more distal radiopaque markers attached to the tubular lattice approximate the open distal end.

16. A method for treating an aneurysm at a bifurcation, the bifurcation comprising a first passageway from a stem blood vessel to a first branch blood vessel and a second passageway from the stem blood vessel to a second branch blood vessel, the aneurysm being positioned opposite the stem blood vessel and between the first and second passageways, and the method comprising:
delivering an implant comprising a tubular lattice comprising an open proximal end, an open distal end, and an interior support structure through a catheter to the aneurysm;
expanding the open distal end and a distal portion of the tubular lattice within a sac of the aneurysm, the open distal end having a first diameter;
extending the interior support structure within the distal portion of the tubular lattice and across a neck of the aneurysm;
positioning a first opening in the tubular lattice across the first passageway, the first opening comprising a first cross sectional area defined by a perimeter of the first opening such that the first cross sectional area extends across a majority of the first passageway;
positioning a second opening in the tubular lattice across the second passageway, the second opening comprising a second cross sectional area defined by a perimeter of the second opening such that the second cross sectional area extends across a majority of the second passageway; and
expanding a proximal portion of the tubular lattice within the stem blood vessel, the proximal portion having a second diameter extending from a distal end of the proximal portion to the open proximal end, the open proximal end having a third diameter,
wherein the first diameter is greater than the second diameter,
wherein the third diameter is greater than the second diameter, and
wherein two narrow sections in a mid body section of the tubular lattice separate the first opening and second opening and extend longitudinally across the mid body section to connect the proximal portion and distal portion, each of the two narrow sections of the mid body section comprising about two smaller cells positioned longitudinally, distal and proximal to each other.

17. The method of claim 16, further comprising:
delivering an embolic implant through the tubular lattice and into the aneurysm sac; and
supporting the embolic implant at the neck of the aneurysm with the interior support structure.

\* \* \* \* \*